(12) United States Patent
Beletskii et al.

(10) Patent No.: US 7,279,296 B2
(45) Date of Patent: Oct. 9, 2007

(54) COMPOSITIONS AND METHODS FOR LIPOPROTEIN UPTAKE ASSAYS

(75) Inventors: Anton Beletskii, Niskayuna, NY (US); Liming Yu, Clifton Park, NY (US); Jason William Castle, Delanson, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 11/305,675

(22) Filed: Dec. 16, 2005

(65) Prior Publication Data

US 2007/0141551 A1    Jun. 21, 2007

(51) Int. Cl.
*C12Q 1/60* (2006.01)
(52) U.S. Cl. .................................................. 435/11
(58) Field of Classification Search ............... None
See application file for complete search history.

(56) References Cited

OTHER PUBLICATIONS

Bernini et al. Arteriosclerosis, Thrombosis, and Vascular Biology. 1995;15(9):1352-1358.*
Esbach et al. Hepathology 1993;18(3):537-545.*
Adie et al. BioTechniques 2002;33:1152-1157.*
CypHer Manual, Amersham, 2003.*
Trigatti B, et al., "Influence of the High Density Lipoprotein Receptor SR-BI on Reproductive and Cardiovascular Pathophysiology," *Proc. Natl. Acad. Sci. U.S.A.*, 96, 9322-7 (1999).
Suzuki H., et al., "A Role for Macrophage Scavenger Receptors in Atherosclerosis and Susceptibility to Infection," *Nature*, 386, 292-296 (1997).
Takahashi K., et al., "Multifunctional Roles of Macrophages in the Development and Progression of Atherosclerosis in Humans and Experimental Animals," *Med. Electron Microsc.*, 35, 179-203 (2002).
Linsel-Nitschke P., et al., "HDL as a Target in the Treatment of Atherosclerotic Cardiovascular Disease," *Nat. Rev. Drug Discov.*, 4, 193-205 (2005).
Lysco P., et al., "Identification of a Small-Molecule, Nonpeptide Macrophage Scavenger Receptor Antagonist," *J. Pharmacol Exp. Ther.*, 289, 1277-85 (1999).
Chow C.W., et al., "Measurement of Phagocytosis and Phagosomal Maturation," p. 15.7.1-15.7.33 in J.S. Bonifacino et al. (Eds.), *Current Protocols in Cell Biology*, John Wiley & Sons, Inc. (2004).
Zhang J.H., et al., "A Simple Statistical Parameter for Use in Evaluation and Validation of High Throughput Screening Assays," *J. Biomol. Screen*, 4, 67-73 (1999).

* cited by examiner

*Primary Examiner*—Ralph Gitomer
*Assistant Examiner*—Bin Shen
(74) *Attorney, Agent, or Firm*—Maureen A. Bresnahan; Jean K. Testa

(57) ABSTRACT

Provided herein are compositions and methods for lipoprotein uptake assay. These compositions and methods may be used for the lipoprotein uptake assays, including high-throughput assays. The disclosed compositions and method may further be used to characterize the activity agents that inhibit or stimulate lipoprotein uptake.

20 Claims, 8 Drawing Sheets

COMPOSITIONS AND METHODS FOR LIPOPROTEIN UPTAKE ASSAYS

FIELD OF THE INVENTION

The present invention relates generally to compositions and methods for lipoprotein uptake assays. More specifically, it relates to pH-sensing dye/lipoprotein conjugates useful in lipoprotein uptake assays and methods for preparing and using these pH-sensing dye conjugates.

BACKGROUND

Lipoproteins play critical role in human health (1-4). Studies in mice have shown that alterations in high-density lipoprotein (HDL) receptor SR-BI expression lead to defects in biliary cholesterol secretion, female fertility, red blood cell development, as well as contributing to the development of atherosclerosis and coronary heart disease (1). Significantly, macrophage type-I and type-II class-A scavenger receptors (SR-A), responsible for uptake of modified low-density lipoprotein (mLDL), have been implicated in the pathological deposition of cholesterol during atherogenesis (2). Thus, the uptake of mLDLs by macrophages with subsequent release of immune mediators and formation of lipid-laden foam cells can lead to the development of atherosclerosis (3). Uptake of native and modified lipoproteins by macrophages and other cell types is an attractive therapeutic target (4-5). However, high-throughput approaches allowing identification of agents that can modulate lipoprotein uptake by macrophages and other cells are lacking.

Current methods rely on labeling of lipoproteins with non-pH-sensing traditional dyes such as BODIPY FL™, DiI and Alexa Fluor™. Assays using such dyes are characterized by low signal-to-noise ratios. Additionally, traditional dyes are susceptible to fluorescence quenching observed in the aggressive and acidic environment of the uptake vesicles (6). Furthermore, these assays are not easily amenable to high-throughput schemes and assays of non-adherent cell types due to requirement for multiple washes needed to achieve accurate measurement of lipoprotein uptake.

Provided herein are methods for lipoprotein labeling with pH-sensing dyes (e.g., CypHer5E™) that demonstrate superior signal-to-noise ratio compared to traditional dyes. Also provided are high-throughput assays for measuring lipoprotein uptake and screening methods for identifying agents that affect lipid accumulation in cell types carrying lipoprotein receptors.

SUMMARY OF THE INVENTION

Provided herein are compositions and methods for lipoprotein uptake assays. These compositions and methods are uniquely suited for the high-throughput lipoprotein uptake assay, as well as the analysis of uptake mediators that inhibit or stimulate lipoprotein uptake.

In one aspect, the present invention provides compositions comprising a pH-sensing dye covalently bound to a lipoprotein to produce a dye-lipoprotein conjugate. In some preferred embodiments the pH-sensing dye comprises 2-[1E,3E)-5-(3-methyl-3-(5-carboxypentyl)-5-sulfo-1,3-dihydro-2H-indol-2-ylidene)-1,3-pentadienyl]-3,3-dimethyl-5-sulfo-1-(4-sulfobutyl)-3H-indolium.

In some embodiments, the lipoprotein component of the conjugate comprises an unmodified lipoprotein or a modified lipoprotein. The lipoprotein may be selected from very-low-density lipoprotein (VLDL), low-density lipoprotein (LDL) and high-density lipoprotein (HDL). Furthermore, the lipoprotein component of the conjugate may comprise modified lipoprotein selected from oxidized, acetylated, glycated, aggregated, and enzymatically degraded lipoprotein.

In another aspect, the present invention provides methods for assaying lipoprotein uptake in a cell population expressing one or more lipoprotein receptors, comprising contacting a disclosed conjugate with a cell population expressing one or more lipoprotein receptors and measuring the level of conjugate uptake. In some embodiments, the conjugate enters the cell through non-receptor-mediated endocytosis. In alternative embodiments the conjugate enters the cell through receptor-mediated endocytosis. In some specific embodiments, the conjugate enters the cell through phagocytosis.

In some embodiments of the disclosed methods, the contacting step comprises culturing the cells in lipoprotein-deficient medium before the contacting the conjugate with the cell population step. In various embodiments, the measuring step may occur 2 hours, 24 hours, or up to 96 hours after contacting the cell population with the dye-lipoprotein conjugate.

In some embodiments, the disclosed methods may further comprise the further contacting the cells with an effector agent before measuring the level of uptake and determining the change in lipoprotein uptake resulting from the effector agent. Exemplary effector agents may include a lipoprotein-uptake inhibitor selected from a polyinosinic acid potassium salt (poly I), a polyguanylic acid potassium salt (poly G), sulfatides from bovine brain, fucoidan, dextran sulfate, and functional variants thereof.

In some embodiments, the lipoprotein uptake is measured for specific cell populations, which may comprise adherent cells selected from macrophage cells, endothelial cells, hepatocytes, and epithelial cells. In further embodiments, the specific cell population expresses a mammalian scavenger receptors selected from scavenger receptors classes A, B, C, D, E, F, or combinations thereof. Thus, the disclosed methods provide methods for assaying lipoprotein uptake in specific cell population that expresses or more mammalian scavenger receptors selected from SR MSR-A I-III, MARCO, CD36, SR-BI, dSR-CI, CD68, LOX-1, SREC, PSR, and SR-PSOX. The cell population may be derived from invertebrate or vertebrate species. Thus, the source of the cell population may be mammalian. In some further embodiments, the cell population comprises inflammatory cells selected from monocytes, macrophage cells, and dendritic cells.

In some embodiments, the disclosed assays may include a measuring step comprising a qualitative comparison of fluorescence of the cell population relative to background fluorescence level. In alternative embodiments, the measuring step comprises a quantitative measurement of fluorescence levels within the cell population. In some preferred embodiments, the measuring step includes exciting the pH-sensing dye with a light source. Although the assays disclosed herein may be performed on multiple samples in series, the disclosed method may be performed on multiple samples in tandem.

DETAILED DESCRIPTION

Figure 1:
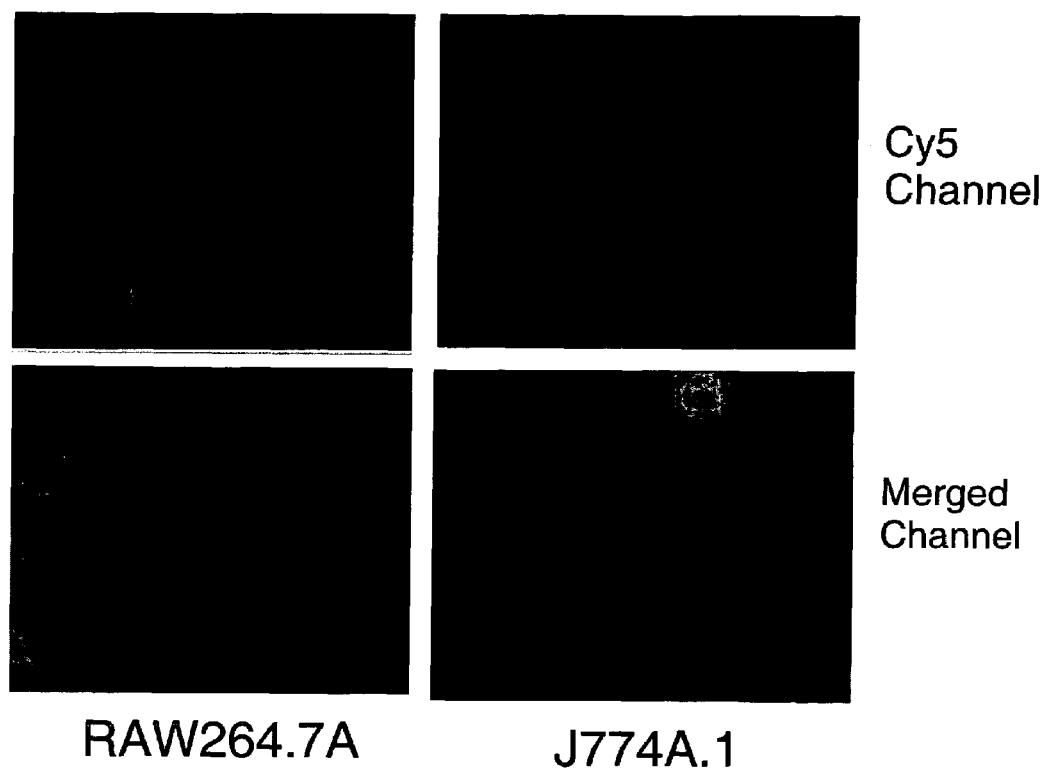
FIG. 1A depicts RAW264.7 mouse macrophages after uptake of pH-sensing-lipoprotein conjugate where the lipoprotein comprises AcLDL.
FIG. 1B depicts J774A.1 mouse macrophages following uptake of pH-sensing-lipoprotein conjugate where the lipoprotein comprises AcLDL.

Provided herein are compositions for dye-lipoprotein conjugates and methods for assaying lipoprotein uptake using the disclosed dye-lipoprotein conjugates.

Definitions

To more clearly and concisely describe and point out the subject matter of the claimed invention, the following definitions are provided for specific terms, which are used in the following description and the appended claims.

As used herein, the term "adherent cell" generally refers to a cell (e.g., macrophage cells) that attaches to a vessel wall (e.g., a non-specialized cell culture-treated polystyrene plastic surface), thereby facilitating the separation of such cells from non-adherent cells (e.g., B cells and T lymphocytes).

As used herein, the term "agonist" of a receptor refers to chemical species that bind the receptor causing a similar functional result as binding of the natural, endogenous ligand of the receptor. That is, the compound must, upon interaction with the receptor produce the same or substantially similar transmembrane and/or intracellular effects as the endogenous ligand. The activity or potency may be less than that of the natural ligand, in which was, the agonist is said to be a "partial agonist," or it can be equal to or greater than the natural ligand, in which case it is said to be a "full agonist." The agonist activity of the scavenger receptor agonists may be assayed by the agonist's ability to competitively inhibit lipoprotein uptake by a cell.

As used herein, the term "dye-lipoprotein conjugate" refers to lipoprotein covalently linked a pH-sensing dye.

As used herein, the term "effector agent" generally refers to any agent that may be contacted with a cell population for determining the effect that the agent has on a lipoprotein uptake in the cell population. Thus, effector agents may include putative or known inhibitors of lipoprotein uptake or putative or known enhancers of lipoprotein uptake.

As used herein, the term "fluorescence" generally refers to the emission of radiation, generally light, from a material during illumination by radiation of usually higher frequency or from the impact of electrons.

As used herein, the terms "lipoprotein" and "lipoproteins" refer to negatively charged compositions that comprise a core of hydrophobic cholesteryl esters and triglyceride surrounded by a surface layer of amphipathic phospholipids with which free cholesterol and apoplipoprotiens are associated. Lipoprotein may be characterized by their density (e.g., very-low-density lipoprotein (VLDL), low-density lipoprotein (LDL) and high density lipoprotein (HDL)), which is determined by their size, the relative amounts of lipid and protein. Lipoproteins may also be characterized by the presence or absence of particular modifications (e.g., oxidization, acetylation, or glycation). In some embodiments, the disclosed pH-sensing lipoprotein conjugates may comprise lipoproteins generated using in vivo approaches (e.g., isolated from blood, through cellular-based or cell-free lysate enzymatic processes). In other embodiments, disclosed pH-sensitive lipoprotein conjugates may comprise lipoproteins generated using in vitro approaches (e.g., through chemical synthesis). In still other embodiments, the lipoprotein may be generated by a combination of in vitro and in vivo approaches.

As used herein, the terms "lipoprotein uptake" and "lipoprotein endocytosis" refer the processes by which eukaryotic cells internalize extracellular fluids, macromolecules, and particles into acidic membrane-bound vesicles. These processes may occur by constitutive endocytosis (i.e., pinocytosis or receptor-mediated endocytosis), phagocytosis, or macropinocytosis.

As used herein the term "lipoprotein-deficient serum" refers to serum (e.g., as used in preparation of culture media) that has been treated to substantially deplete the lipoprotein concentration (e.g., by centrifugation or affinity chromatography). Similarly, the term "lipoprotein-deficient media" refers to media that comprises lipoprotein-deficient serum or has otherwise been depleted of serum components.

As used herein, the term "lipoprotein-receptor-expressing-cell" means any cell expressing lipoprotein receptors. A lipoprotein-receptor-expressing-cell may express endogenous lipoprotein receptors or may be engineered to express exogenous lipoprotein receptors.

As used herein the term "modified LDLs" and the abbreviation "mLDLs" generally refer to AcLDL or oxLDL.

As used herein, the term "pH-sensing dye" refers to the dye that increases fluorescence with the decrease of physiological range of pH from 9 to 5. Illustrative pH-sensing cyanine dyes include the cyanine dyes disclosed in International Patent Application PCT/US00/15682, incorporated herein by reference in its entirety. In some embodiments the pH-sensing cyanine dye comprises a mono N-hydroxysuccinimide (NHS) ester. The pH-sensing dyes used herein comprise a pair of heterocycles linked by a polymethine bridge, with tertiary nitrogen atoms on both heterocyclic rings. In preferred embodiments, the pH-sensing dye demonstrates an absorbance maximum of about 645 nm and an emission maximum of about 663 nm.

As used herein, the term scavenger receptor refers to receptors specifically binding mLDL. Generally, mLDL uptake occurs when the mLDL comes into contact with cells expressing a scavenger receptor on their surface. For example, mouse macrophages express scavenger receptors capable of binding and internalizing LDLs. Such mouse scavenger receptors may include, for example, MSR-A I-III, MARCO, CD36, SR-BI, dSR-CI, CD68, LOX-1, SREC, PSR, and SR-PSOX.

As used herein the phrase "signal-to-noise ratio" refers to the ratio of fluorescence level within the cells after dye-lipoprotein conjugate uptake to the fluorescence level in the assay media. In embodiments where the cells are suspended in a medium or adhered to a culture vessel medium, the noise (i.e., background level of fluorescence) corresponds to the fluorescence detected in the medium. In some embodiments, using the disclosed assays and compositions, signal-to-noise ratio is about 4-5.

Specific Embodiments

In lipoprotein-dye conjugates, the pH-sensing dye is covalently bound to the protein portion of the lipoprotein complex while lipophilic dyes (e.g., DiI) diffuse into the hydrophobic portion of the lipoprotein conjugate without forming a covalent bond with lipoprotein. Covalent bonding of the pH-sensing dye to the lipoprotein provides greater stability of the reagent and ensures that dye portion of the conjugate is not extracted during subsequent manipulations of the cells.

The disclosed assays are suitable for the study of physiological conditions associated with lipoprotein uptake. Conditions associated with lipoprotein uptake may include inflammatory disease (e.g., autoimmune conditions such as arthritis), vascular disease (e.g., atherosclerosis), and defects of lipoprotein metabolism in the liver. The disclosed assays do not require washing steps. Thus, they may be performed on both adherent and non-adherent cells with decreased effort compared to the traditional assays. Furthermore, the disclosed assays may be automated for high-throughput screening to thereby provide for cell-based functional assays that are useful, for example, in drug discovery.

The assays employ a pH-sensing cyanine dye, which is minimally fluorescent at neutral pH outside the cell, but highly fluorescent in the acidic environment (pKa ~7.3; excitation peak 650 nm/emission peak 670 nm). In most instances, the lipoproteins or modified lipoproteins are taken up by cell-surface receptors through the process of receptor-mediated endocytosis. Once internalized, lipoproteins are transported to highly acidic vesicles. When labeled with CypHer5E™ dye, lipoproteins are minimally fluorescent at neutral pH outside the cell, but highly fluorescent in the acidic environment of the uptake vesicle. This translates into high signal-to-noise ratio compared to traditional dyes that are equally fluorescent inside or outside the cell. Additionally, the disclosed methods eliminate washing steps required for removal of excess of labeled lipoprotein in the media at the end of the protocol. The absence of washing steps in our protocol allows development of true high-throughput assays for lipoprotein uptake.

The disclosed compositions and methods also provide a synergy between assay biology and automation feature of cellular analyzers (e.g., IN Cell Analyzer™ 1000 by GE Healthcare) for quantitative analysis by omitting all of the intermediary washing steps required for traditional assays between dye-lipoprotein complex or conjugate addition and measurement in the analyzer. Additionally routine signal-to-background ratio for CypHer5E-lipoprotein conjugates is 4-5 allowing robust software image analysis and accurate measurement of mLDL uptake by analyzer, while signal-to-background ratios of 1.3-1.5 observed with traditional dyes make robust and accurate measurement unfeasible.

Preparation of the pH-sensitive Cyanine Dye Conjugates

Lipoprotein is conjugated to a mono N-hydroxysuccinimide (NHS) ester dye (e.g., CypHer5E™) that reacts with free amino groups on lipoprotein. CypHer5E™ mono NHS ester reactivity with buffer was minimized by the use of buffer without free amino groups. In some embodiments, using the disclosed assays and compositions, 0.1 M to 1M sodium bicarbonate buffer was used. In other embodiments, using the disclosed assays and compositions, 0.1 M to 0.5 M sodium bicarbonate buffer was used. In yet other embodiments, using the disclosed assays and compositions, 0.09 M to 0.11 M sodium bicarbonate buffer was used. Another commonly used buffer lacking free amino groups is sodium borate buffer.

Buffer pH was optimized to allow reactivity of the mono NHS ester with lipoprotein through maximal exposure of free amino groups on protein to mono NHS ester. Most of the amino groups in proteins are in protonated form at neutral pH of 7, and are not available for conjugation with Mono N-hydroxysuccinimide (NHS) ester of the dye. We found that the basic pH of the carbonate buffer allows for maximum labeling of lipoprotein. In some embodiments, using the disclosed assays and compositions, pH 8 to pH 11 sodium bicarbonate buffer was used. In other embodiments, using the disclosed assays and compositions, pH 8 to pH 11 sodium bicarbonate buffer was used. In yet other embodiments, using the disclosed assays and compositions, pH 8.9 to pH 9.2 sodium bicarbonate buffer was used.

Molar Ratios. We found that respective molar amounts of dye lipoprotein need to be optimized for imaging of dye-lipoprotein conjugate using standard commercially available imaging equipment. In some embodiments, using the disclosed assays and compositions, 10-fold to 220-fold molar excess of dye to lipoprotein was used. In other embodiments, using the disclosed assays and compositions, 50-fold to 110-fold molar excess of dye to lipoprotein was used. In yet other embodiments, using the disclosed assays and compositions, 200-fold to 220-fold molar excess of dye to lipoprotein was used.

Purification The dye-lipoprotein conjugate may be purified by size exclusion chromatography and nanofiltration thereby separation of the conjugate from excess of the free unreacted dye. Purification step or steps improves high signal-to-noise ratio in subsequent assays. Alternative purification methods include without limitation, methods based on molecular weight differences or size differences between the dye monomer and the dye-lipoprotein conjugate, for example dialysis.

Lipoprotein Uptake Assays

The following assays may be performed using any technique employing a device comprising a fluorimeter including: flow cytometry, microscopy, optical measurement of fluorescence, and combinations thereof.

Figure 5:
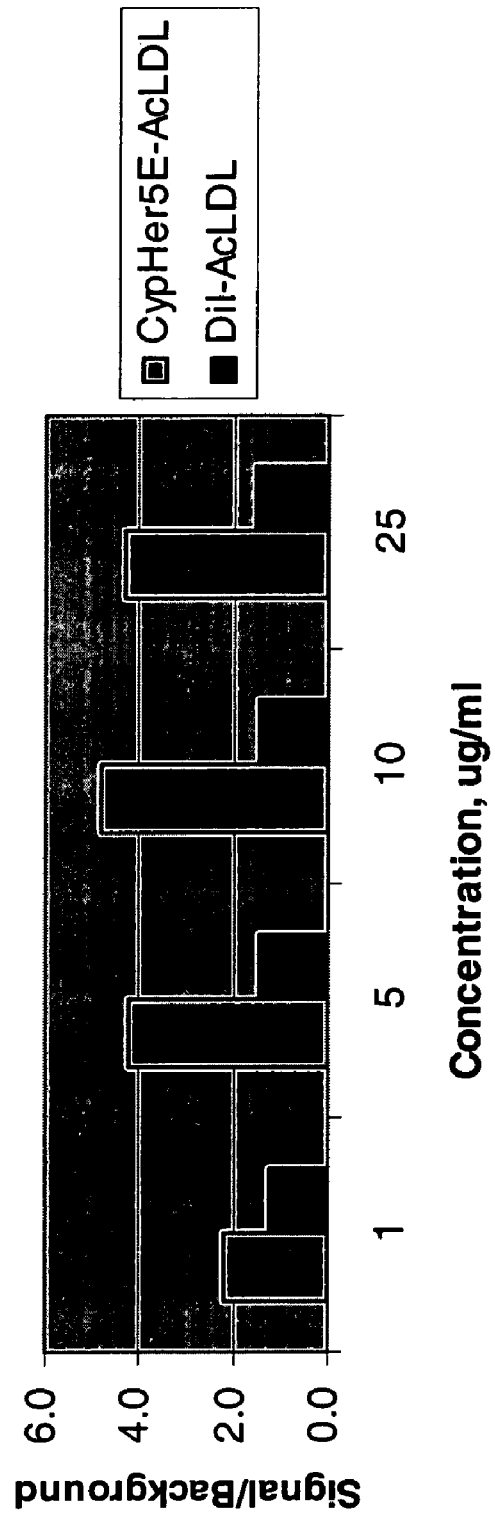
FIG. 5 is a graph comparing signal-to-background (S/B) ratios for measurement of AcLDL uptake using either CypHer5E™-AcLDL or DiI-AcLDL at various concentrations.

1,1'-dioctadecyl-3,3,3',3'-tetramethylindocarbocyanine perchlorate-labeled AcLDL (DiI-AcLDL) has been used to identify and mark endothelial and macrophage-like cells in primary cultures and tissues because of presence on their surface receptors for AcLDL. Because this dye is bound non-covalently to the AcLDL, the binding is unstable and steps must be taken to avoid losing the dye portion of the complex when performing a protocol using the non-covalent entity. In contrast, the covalent bonding of the pH-sensing dye to the lipoprotein reduces the risk of dye loss in subsequent manipulations of cells or tissues and lends itself to the development of novel staining techniques. This method not only eliminates the need for multiple washing steps in the labeling protocol, it also decreases loss of cells and material during the assays. Furthermore, the reduction or absence of washing steps makes the disclosed assays amenable to use on non-adherent cells as well as adherent cells, without the need for a wash solution removal which can substantially disturb those cells adhered to the vessel surface or nonadherent cells by, for example, aspiration (FIGS. 1 and 5).

Figure 2:
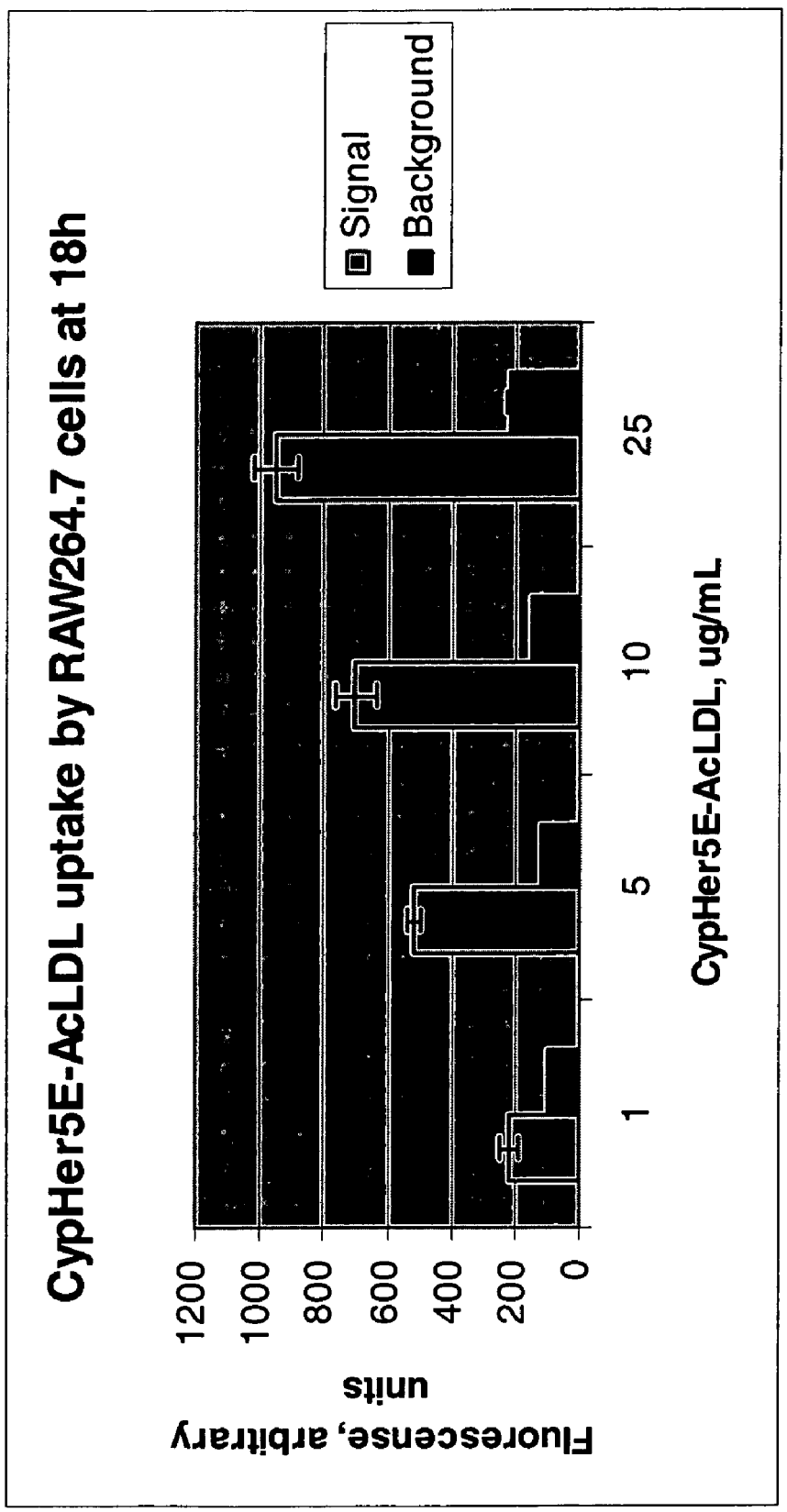
FIG. 2 is a graph showing the levels of fluorescence within RAW264.7 mouse macrophages and the background level of fluorescence following incubation with various concentrations of pH-sensing-lipoprotein conjugate where the lipoprotein comprises AcLDL.
Figure 4:
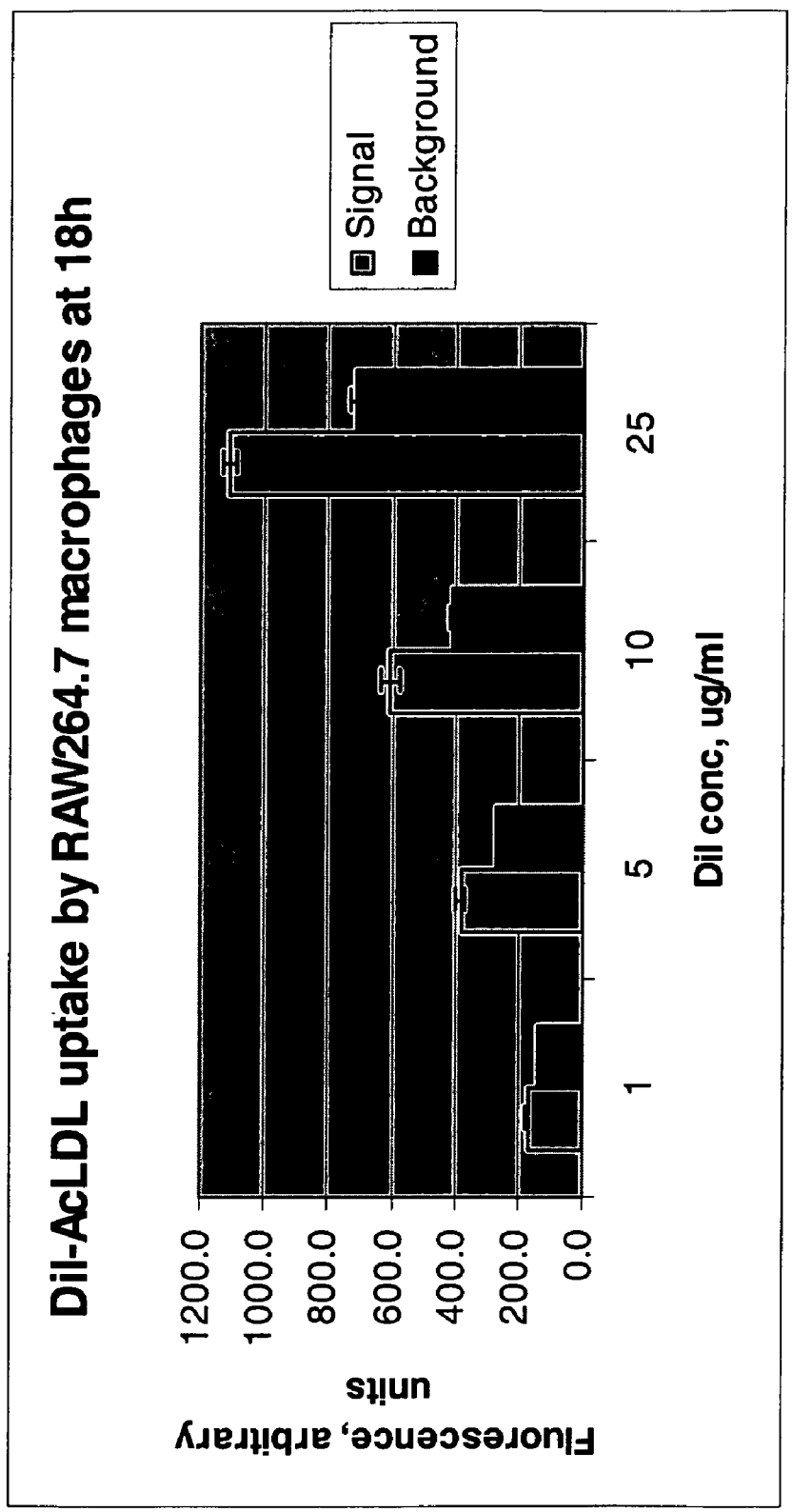
FIG. 4 is a graph showing the relative level of fluorescence within RAW264.7 mouse macrophages compared the background following incubation with various concentrations of DiI-AcLDL.

CypHer5E-AcLDL demonstrates a superior signal-to-background ratio of 2 to 5 (FIG. 2). The signal-to-background ratio for CypHer5E-lipoprotein conjugate is compared to the signal-to-background ratio for DiI-lipoprotein complex when same protocol is applied. Specifically, the DiI AcLDL complex assay was identical to CypHer5E-AcLDL assay as described in the examples, except that equal amount of DiI AcLDL complex was added to cells in place of CypHer5E-AcLDL conjugate. The results for DiI AcLDL complex are shown in FIG. 4. These results demonstrate that signal-to-background ratio of CypHer5E conjugate is from 122% to 277% higher than signal-to-background ratio of DiI AcLDL complex between 1 µg/ml and 25 µg/ml concentration of the lipoprotein (FIG. 5).

Figure 3:
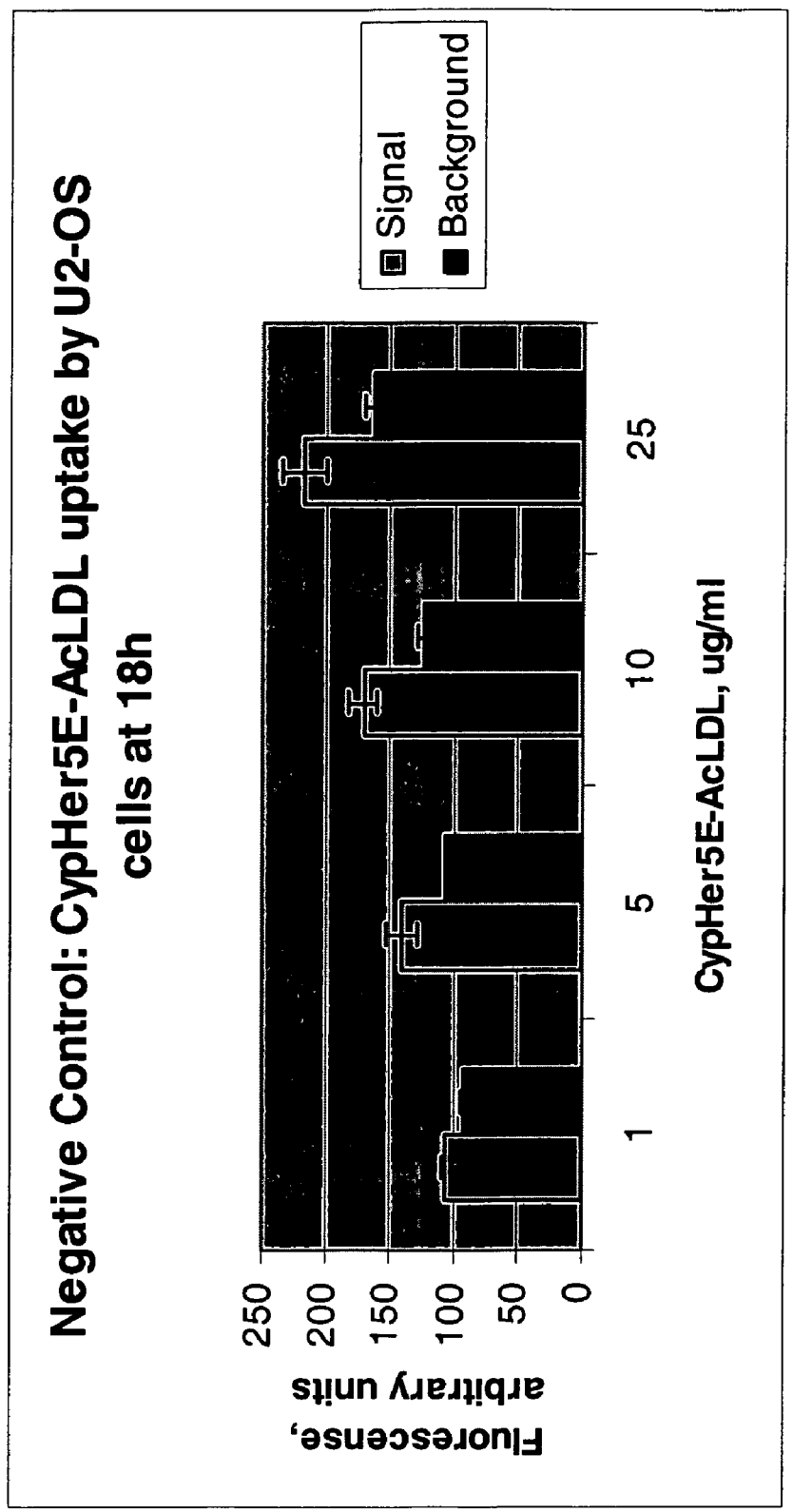
FIG. 3 is a graph depicting levels of fluorescence within U-2 OS human osteosarcoma cells that lack molecular machinery for AcLDL uptake and the level of fluorescence in the background after incubation with different concentrations of CypHer5E™-AcLDL.

For cells not expressing corresponding lipoprotein uptake receptor, uptake of CypHer5E-lipoprotein conjugate is minimal when compared to the cells expressing corresponding lipoprotein uptake receptor (Compare signal in FIGS. 2 and 3). Moreover, signal is statistically comparable to the background for cells not expressing corresponding lipoprotein uptake receptor (FIG. 3). These results demonstrate that conjugation of dye to lipoprotein does not lead to non-specific uptake of dye-lipoprotein conjugate.

EXAMPLES

Practice of the invention will be still more fully understood from the following examples, which are presented herein for illustration only and should not be construed as limiting the invention in any way. Table 1 lists the materials used in the following Examples, along with manufacturer information.

TABLE 1

Materials used in the Examples.

| Material | Supplier | Catalogue # |
|---|---|---|
| RAW264.7 Mouse Macrophages | ATCC | TIB-71 |
| J774A.1 Mouse Macrophages | ATCC | TIB-67 |
| U-2 OS Human Osteosarcoma | ATCC | HTB-96 |
| Dulbecco's Modified Eagle Medium | Invitrogen | 10564-011 |
| Fetal Bovine Serum | Hyclone | SH30070.30 |
| Fetal Bovine Lipoprotein Deficient Serum (FBLDS) | Intracel | RP-056 |
| CellTracker Green ™ | Invitrogen | C2925 |
| CypHer5E ™ Mono NHS Ester | GE Healthcare | PA15401 |
| Phosphate Buffered Saline (PBS) | Invitrogen | 10010-023 |
| Sodium Bicarbonate | Sigma | S5761 |
| Dimethyl sulfoxide (DMSO) | Sigma | D4540 |
| Tris(hydroxymethyl)aminomethane (Tris) | Sigma | T6791 |
| Ethylenediaminetetraacetic acid (EDTA) | Sigma | E6758 |
| Human Low Density Lipoprotein (LDL) | Intracel | RP-032 |
| Human Oxidized Low Density Lipoprotein (OxLDL) | Intracel | RP-047 |
| Human Acetylated Low Density Lipoprotein (AcLDL) | Intracel | RP-045 |
| DiI AcLDL Complex | Invitrogen | L-3484 |
| Polyinosinic acid potassium salt (poly I) | Sigma | P4154 |
| Polyguanylic acid potassium salt (poly G) | Sigma | P4404 |
| Sulfatides from bovine brain | Sigma | S1006 |
| Dextran Sulfate MW 500,000 (Dex SO$_4$) | Sigma | D8906 |
| D-Salt ™ Dextran Desalting Columns 5 ml | Pierce | 43230 |
| Nanosep ™ 10K Omega Columns | Pall Corporation | OD010C33 |
| InCell 1000 Analyzer ™ | GE Healthcare | 25-8010-26 |
| InCell 3000 Analyzer ™ | GE Healthcare | 25-8010-11 |
| Developer Image Analysis Software ™ | GE Healthcare | 25-8098-26 |
| ViewPlate ™ 96-well plate | PerkinElmer | 6005182 |

Example 1

Preparation of LDL and AcLDL Conjugated to CypHer5E™ Dye

200 µl of acetylated low density lipoprotein (AcLDL; 2.5 mg/ml) were mixed with 56 µl of 0.89 M sodium bicarbonate (pH 9.0) and 244 µl of phosphate buffered saline (PBS; pH 7.2) containing 0.3 mM ethylenediaminetetraacetic acid (EDTA) for a total volume of 500 µl. 1 mg of CypHer5E™ dye mono NHS ester (2-[1E,3E)-5-(3-methyl-3-(5-carboxypentyl)-5-sulfo-1,3-dihydro-2H-indol-2-ylidene)-1,3-pentadienyl]-3,3-dimethyl-5-sulfo-1-(4-sulfobutyl)-3H-indolium) was dissolved in 100 µl of dimethyl sulfoxide (DMSO). From 1 µl to 20 µl of CypHer5E™ solution were added to AcLDL mix in a typical experiment. The reaction mixture was gently rocked for 1 hour at room temperature in the dark before the reaction was stopped by addition of 50 µl of 1M tris (hydroxymethyl) aminomethane (Tris).

The labeled AcLDL was separated from the excess of un-conjugated CypHer5E™ dye by exclusion chromatography using D-Salt™ Dextran Desalting Columns according to the manufacturer's suggestions. In brief, the columns were equilibrated with PBS containing 0.3 mM EDTA, reaction mixture containing labeled AcLDL and free dye was applied to equilibrated column, and eluted by PBS with 0.3 mM EDTA. The eluted fraction containing CypHer5E™-labeled AcLDL (CypHer5E™-AcLDL) but not free dye was collected for further purification.

CypHer5E™-AcLDL was further purified and concentrated using Nanosep™ 10K Omega Columns according to the manufacturer's suggestions. The CypHer5E™-AcLDL was resuspended in PBS with 0.3 mM EDTA at 2.5 mg/ml.

Example 2

Culture and Cell-Specific Staining of RAW264.7 Mouse Macrophages, J774A.1 Mouse Macrophages, U-2 OS Human Osteosarcoma Cells RAW264.7 Mouse Macrophages, J774A.1 Mouse Macrophages, U-2 OS Human Osteosarcoma Cells were seeded in standard cell culture flasks and cultured in Dulbecco's Modified Eagle Medium (DMEM) with 10% fetal bovine serum (FBS) until about 70% to about 80% confluent. On the day of the assay, the cells were washed twice with serum-free DMEM, and incubated for 30 minutes in cell culture incubator in DMEM containing 1 μM Cell Tracker Green dye. After staining with Cell Tracker Green dye, cells were washed three times with serum-free DMEM, scraped from tissue culture flask, and resuspended in DMEM with 12.5% Fetal Bovine Lipoprotein Deficient Serum (FBLDS) at 250,000 cells/ml.

Example 3

Assaying AcLDL Uptake

80 μl of Cell Tracker Green-labeled cells at 250,000 cells/ml were added to each well of ViewPlate 96-well plate in DMEM with 12.5% Fetal Bovine Lipoprotein Deficient Serum (FBLDS). For inhibitor studies, 10 μl of 10-fold stock of the inhibitor in DMEM containing 10% dimethyl sulfoxide (DMSO) were added to each well. 10 μl of DMEM containing 10% DMSO were added for control wells. Cells were pre-incubated for 30 minutes at 37° C. in cell culture incubator in the presence of the inhibitor before addition of labeled AcLDL. At the end of pre-incubation period, 10 μl of 100 μg/ml CypHer5E™-AcLdL solution were added to each well. The incubation continued for another 2 to 18 hours at 37° C. in cell culture incubator before imaging. The DiI AcLDL complex assay was identical to CypHer5E™-AcLDL assay except that DiI AcLDL complex was added to cells in place of CypHer5E™-AcLDL conjugate.

Example 4

Microscopy and Image Analysis

Following incubation, images of CypHer5E™m-AcLDL uptake were acquired on IN Cell Analyzer 1000 or 3000 (GE Healthcare) using a 10× or 20× objective and FITC/Cy5 excitation/emission filters. Analysis was performed using Granularity Analysis and Object Intensity Analysis Modules within IN Cell Analyzer™ system software suite or using Developer™ Image Analysis software.

FIG. 1 demonstrates uptake of CypHer5E™-AcLDL by RAW264.7A mouse macrophage cells and by J774A.1 mouse macrophage cells. In the photograph, cells are labeled with Cell Tracker Green dye while AcLDL is conjugated to the red CypHer5E™m dye. Both cell lines are known to express a diverse set of AcLDL receptors on their surface and demonstrated robust uptake of CypHer5E™-AcLDL conjugate (FIGS. 1 and 2). This experiment demonstrates that labeling conditions and conjugation of CypHer5E™ to the modified apoprotein part of AcLDL molecule did not significantly affect specific recognition of AcLDL by the receptors. Uptake was minimal and comparable to background for U-2 OS human osteosarcoma cell line that does not express receptors for AcLDL (FIG. 3).

Example 5

Signal-to-Background Ratio for CypHer5E™-AcLDL Uptake Assay

CypHer5E™ dye is 3 to 20 times more fluorescent in the acidic environment of the intracellular vesicles than at neutral pH outside the cell (pKa ~7.3; excitation peak 650 nm/emission peak 670 nm). CypHer5E™ dye fluorescence is enhanced by the acidic conditions of lipoprotein-containing intracellular vesicles after receptor-mediated lipoprotein after the CypHer5E™-AcLDL is internalized. Additionally, neutral pH in the cell culture media results in greatly reduced background from non-internalized CypHer5E™-AcLDL and leads to increased assay robustness.

The signal-to-background ratio CypHer5E™-AcLDL conjugate was compared to the signal-to-background ratio for DiI AcLDL complex in RAW264.7A mouse macrophages. The signal-to-background ratio CypHer5E™-AcLDL conjugate is from 122% to 277% higher than signal-to-background ratio for DiI AcLDL complex between 1 μg/ml and 25 μg/ml concentration of the lipoprotein (FIG. 5). FIG. 2 is a graph depicting levels of fluorescence within RAW264.7 mouse macrophages (signal) and in the media (background) after incubation with different concentrations of CypHer5E™-AcLDL for 18 hours. The results indicate that increasing concentration of CypHer5E™-AcLDL lead to progressively stronger signal with minimal increase in the background. In comparison, DiI background fluorescence increases with concentration and results in lower signal-to-background ratios than for CypHer5E at identical concentration. (FIG. 4). Overall, signal-to-background ratio was lower for CypHer5E™-AcLDL conjugate when compared to DiI-AcLDL complex across all concentrations tested (FIG. 5).

Example 6

Figure 6:
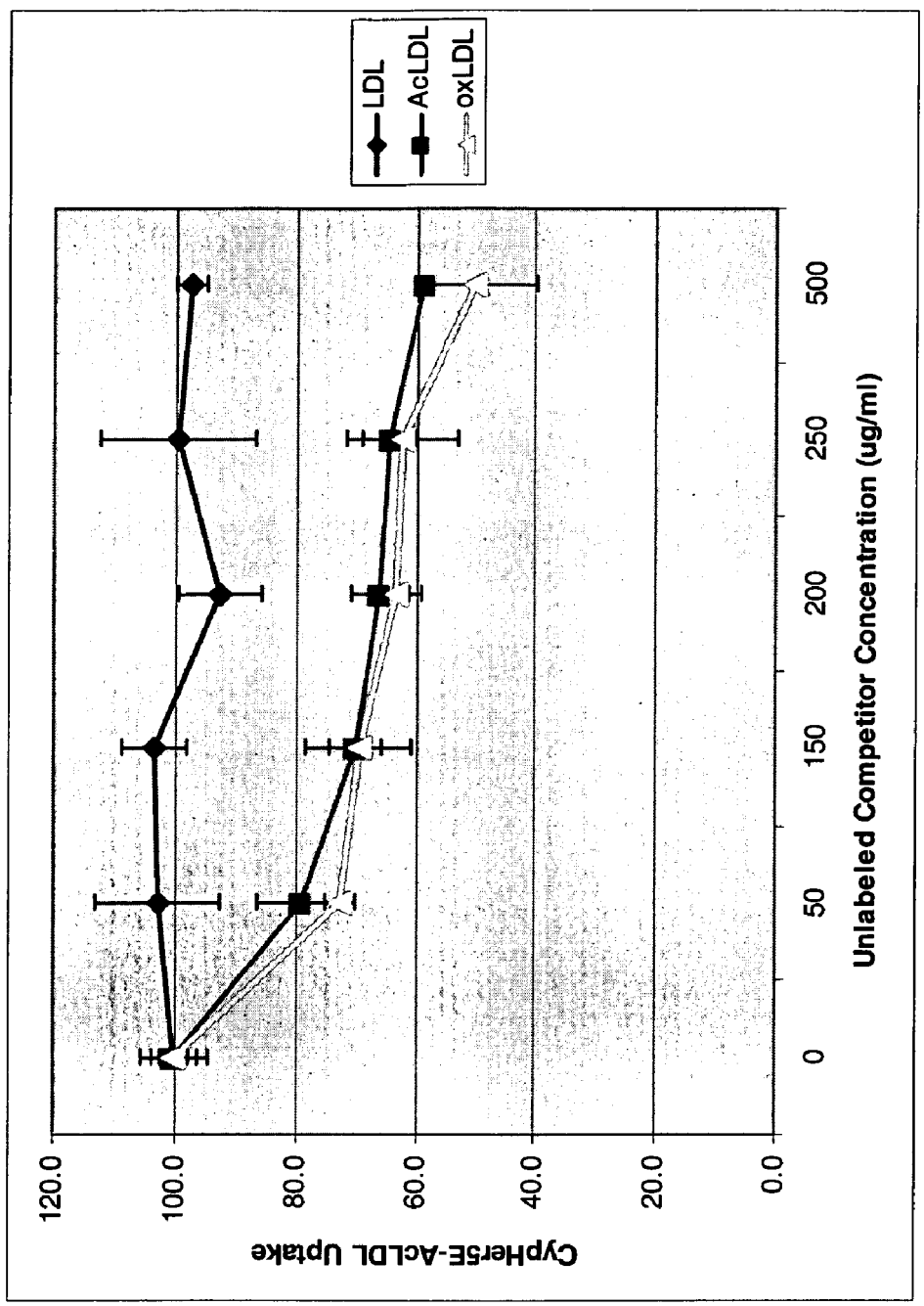
FIG. 6 shows competitive inhibition of pH-sensitive cyanine dye conjugate uptake by oxidized LDL (OxLDL), acetylated LDL (AcLDL), and unmodified LDL in RAW264.7 mouse macrophages. Unmodified LDL shows no uptake, and serves as a negative control in this example because RAW264.7 macrophages do not have the receptor for unmodified LDL.

Competitive Inhibition of CypHer5E™-AcLDL Uptake by Unlabeled AcLDL and Ox-LDL in Mouse Macrophage Cells To demonstrate the utility of CypHer5E™-AcLDL conjugate for assaying inhibition of AcLDL uptake, we measured the competitive inhibition of CypHer5E™-AcLDL uptake in an excess of unlabeled mLDL. Two types of mLDLs (i.e., unlabeled AcLDL and unlabeled OxLDL) were independently shown to inhibit uptake of CypHer5E™-AcLDL conjugate in competitive manner from 20-50% across a wide range of concentrations (FIG. 6). The presence of unmodified LDL did not lead to inhibition of CypHer5E™-AcLDL uptake, because unmodified LDL is not a ligand for scavenger receptors responsible for uptake of modified LDL (FIG. 6).

Example 7

Figure 7:
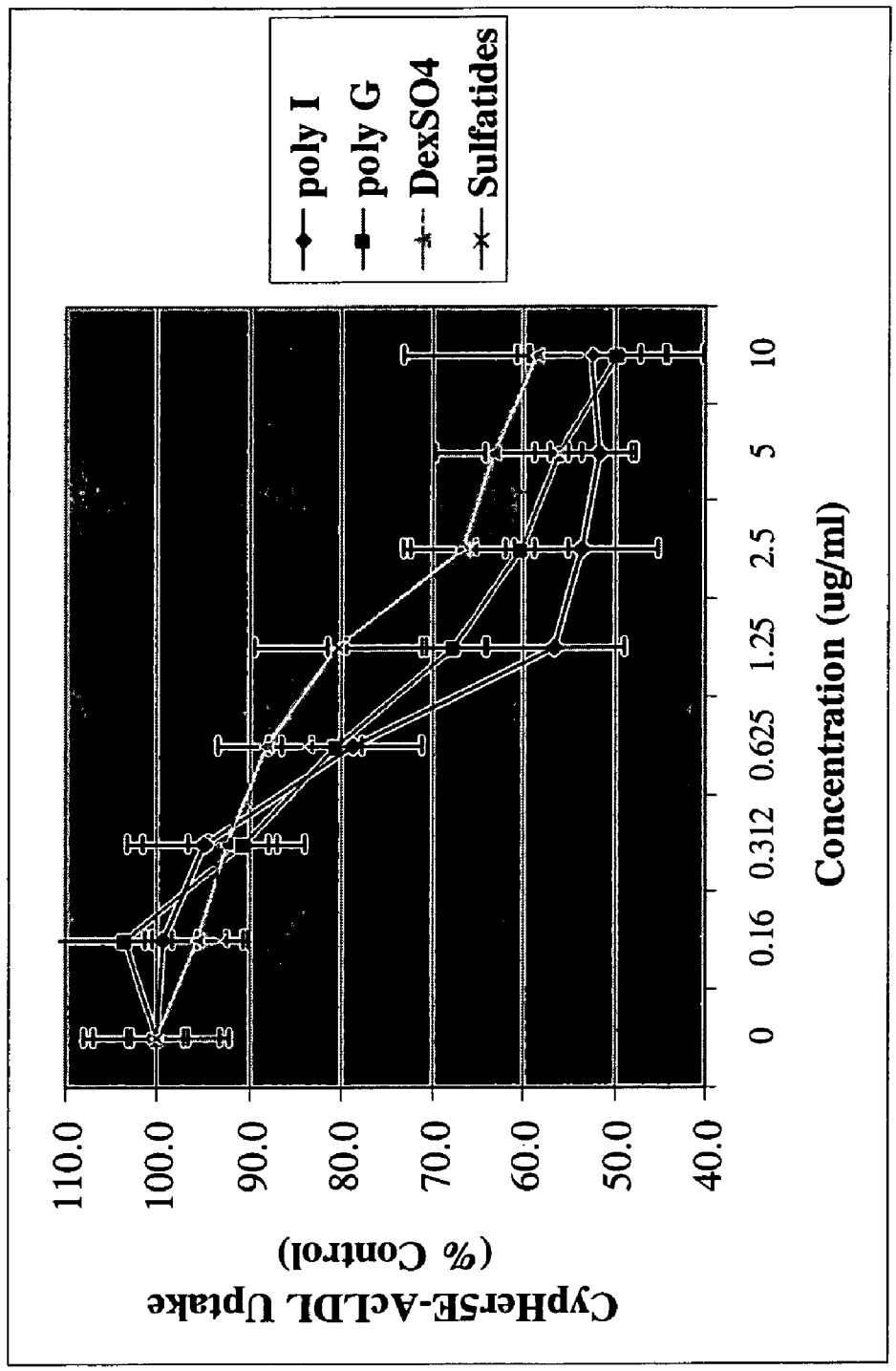
FIG. 7 shows inhibition of pH-sensing cyanine dye conjugate uptake in RAW264.7 mouse macrophages by known inhibitors of scavenger receptor A (SR-A, CD204): polyinosinic acid potassium salt (poly I), polyguanylic acid potassium salt (poly G), dextran sulfate (Dex $SO_4$), and sulfatides.

Inhibition of CypHer5E™-AcLDL Uptake by Known Scavenger Receptor-A (SR-A) Ligands This example demonstrates that the CypHer5E™-AcLDL uptake assays disclosed herein are useful for studies directed to the identification of inhibitors of mLDL uptake by SR-A. SR-A has been identified as a target for agents designed to treat or reduce the incidence of atherosclerosis. Known SR-A ligands were shown to inhibit CypHer5E™-AcLDL uptake at concentrations of 0.5-1.1 μg/ml inhibitory concentrations comparable to known inhibitory concentrations for these inhibitors (FIG. 7).

Example 8

A High-Throughput CypHer5E™-AcLDL Uptake Assay System

This example demonstrates that the assays described herein are useful for high-throughput assay schemes. The CypHer5E™-AcLDL uptake assay was implemented in a 96-well plate (ViewPlate™, PerkinElmer) platform. Analysis of CypHer5E™-AcLDL uptake was performed with an automated cellular analyzer IN Cell Analyzer™ (GE Healthcare). Images taken by IN Cell Analyzer™ were then processed by automated image analysis and quantitation software within IN Cell Analyzer™ system software suite (Granularity Analysis and Object Intensity Analysis Modules) or using Developer™ Image Analysis software. The data shown in FIGS. 2-8 were generated using this workflow with the use of Developer™ Image Analysis software. Thus, the implementation of the assay system in the 96-well format in combination with the automatic imaging and data analysis provides high-throughput AcLDL uptake assay systems that can be used for the large-scale discovery and evaluation of mLDL uptake mediators. Because image acquisition is performed without disturbing the assay system it can also provide data for multiple time-points in a single experiment.

Figure 8:
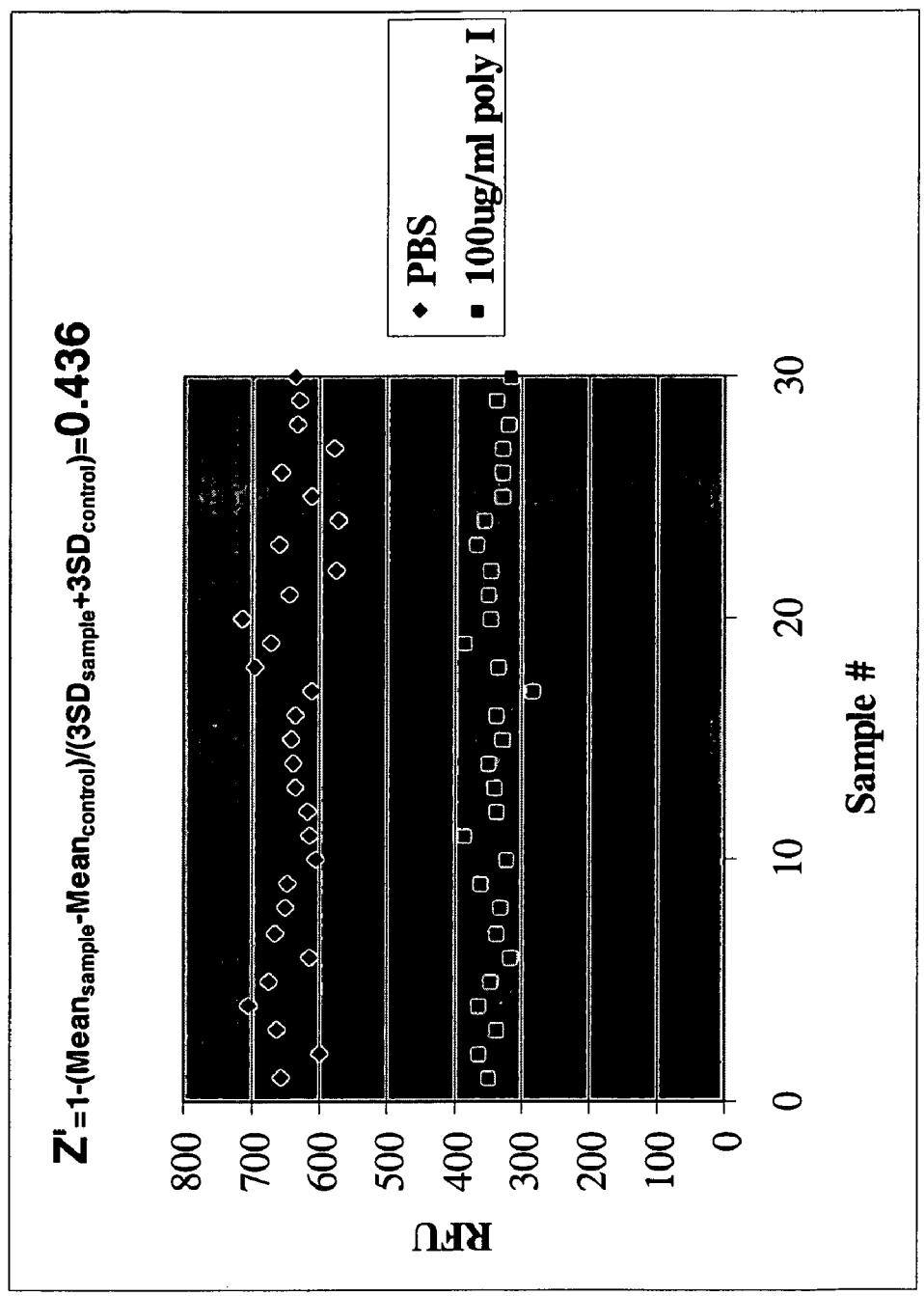
FIG. 8 shows determination of Z-factor (7) for high-throughput CypHer5E-AcLDL uptake assay performed in 96-well plate containing RAW264.7A macrophages by treating 30 wells of a with 100 µM poly I while leaving another 30 wells untreated (FIG. 8).

The suitability of the system for high-throughput screening was demonstrated by determining the Z-factor for multiple samples. Specifically, 30 wells of a 96-well plate containing RAW264.7A macrophages with 100-μM poly I, while leaving another 30 wells untreated (FIG. 8). The Z-factor is reflective of both the assay signal dynamic range and the data variation associated with the signal measurements, and therefore is suitable for assay quality assessment. As can be seen from FIG. 8, Z-factor of 0.43 for the assay described here approaches value of 0.5 commonly considered adequate for high-throughput cellular screening, and is well above minimum of 0.2-0.3 required for meaningful cell-based assays.

The following references are incorporated herein by reference.

1. Frigate B., Rayburn H., Vinals M., et al., "Influence of the high density lipoprotein receptor SR-BI on reproductive and cardiovascular pathophysiology", Proc. Natl. Acad. Sci. USA, 96, 9322-7 (1999).
2. Suzuki H., Kurihara Y., Takeya M., et al., "A role for macrophage scavenger receptors in atherosclerosis and susceptibility to infection," Nature, 386, 292-296 (1997).
3. Takahashi K., Takeya M., and Sakashita N., "Multifunctional roles of macrophages in the development and progression of atherosclerosis in humans and experimental animals," Med. Electron Microsc., 35, 179-203 (2002).
4. Linsel-Nitschke P. and Tall A., "HDL as a target in the treatment of atherosclerotic cardiovascular disease," Nat. Rev. Drug Discov., 4, 193-205 (2005).
5. Lysco P., Weinstock J., Webb C., Brawner M., and Elshourbagy N., "Identification of a small-molecule, non-peptide macrophage scavenger receptor antagonist" J. Pharmacol. Exp. Ther., 289, 1277-85 (1999).
6. Chow C. W., Downey G. P., and S. Grinstein. Measurement of phagocytosis and phagosomal maturation, p. 15.7.1-15.7.33. In J. S. Bonifacino et al. (Eds.), Current Protocols in Cell Biology. John Wiley & Sons Inc. (2004)
7. Zhang J. H., Chung T. D., and K. R. Oldenburg, "A Simple Statistical Parameter for Use in Evaluation and Validation of High Throughput Screening Assays," J. Biomol. Screen, 4, 67-73 (1999).

We claim:

1. A method for assaying lipoprotein uptake in a cell population expressing one or more lipoprotein receptors, comprising contacting a conjugate having pH-sensing cyanine dye covalently bound to a lipoprotein, wherein the pH-sensing cyanine dye is minimally fluorescent at neutral pH and maximally fluorescent at acidic pH with a cell population expressing one or more lipoprotein receptors and measuring the level of conjugate uptake.

2. The method of claim 1, wherein the conjugate enters the cell through receptor-mediated endocytosis.

3. The method of claim 1, wherein the contacting step further comprises culturing the cells in lipoprotein-deficient medium, before the contacting the conjugate with the cell population step.

4. The method of claim 1, wherein the measuring step is occurs within 96 hours after the contacting step.

5. The method of claim 1, wherein the measuring step occurs within 24 hours after the contacting step.

6. The method of claim 1, wherein the measuring step occurs within 2 hours the contacting step.

7. The method of claim 1, further comprising the steps of measuring the level of lipoprotein uptake in a cell population, contacting the cell population with an effector agent, and measuring the level of lipoprotein uptake following the contacting with the effector agent, and determining the change in lipoprotein uptake resulting from the effector agent.

8. The method of claim 7, wherein the effector agent comprises a lipoprotein-uptake inhibitor selected from a polyinosinic acid potassium salt (poly I), a polyguanylic acid potassium salt (poly G), sulfatides from bovine brain, fucoidan, and dextran sulfate.

9. The method of claim 1, wherein the cell population comprises adherent cells selected from macrophage cells, endothelial cells, hepatocytes, and epithelial cells.

10. The method of claim 1, wherein the cell population expresses a mammalian SR selected from SR classes A, B, C, D, E, F, or combinations thereof.

11. The method of claim 1, wherein the cell population expresses one or more mammalian scavenger receptors selected from SR MSR-A I-III, MARCO, CD36, SR-BI, dSR-CI, CD68, LOX-1, SREC, PSR, and SR-PSOX.

12. The method of claim 1, wherein the cell population is comprises mammalian cells.

13. The method of claim 1, wherein the cell population comprises inflammatory cells selected from monocytes, macrophage cells, and dendritic cells.

14. The method of claim 1, wherein the measuring step comprises a qualitative comparison of fluorescence of the cell population relative to background fluorescence level.

15. The method of claim 1, wherein the measuring step comprises a quantitative measurement of fluorescence levels within the cell population.

16. The method of claim 1, wherein the method is performed on multiple samples in tandem.

17. The method of claim 1, wherein optimal pH of the pH-sensing dye covalently bound to the lipoprotein is about 5.

18. The method of claim 1, wherein the level of conjugate uptake is measured by determining the fluorescence intensity of the cell population.

19. The method of claim 18, wherein the signal-to-noise ratio of the fluorescence intensity of the cell population contacted with the pH-sensing dye covalently bound to the lipoprotein is about 4 to about 5.

20. The method of claim 1, wherein the pH-sensing dye comprises 2-[1E,3E)-5-(3-methyl-3-(5-carboxypentyl)-5-sulfo-1,3-dihydro-2H-indol-2-ylidene)-1,3-pentadienyl]-3,3-dimethyl-5-sulfo-1-(4-sulfobutyl)-3H-indolium.

* * * * *